(12) United States Patent
Krishnamurthy

(10) Patent No.: US 11,859,233 B2
(45) Date of Patent: *Jan. 2, 2024

(54) RAPID MICROBIAL DETECTION

(71) Applicant: Rajesh Krishnamurthy, Germantown, MD (US)

(72) Inventor: Rajesh Krishnamurthy, Germantown, MD (US)

(73) Assignee: 3I DIAGNOSTICS, INC., Germantown, MD (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/681,899

(22) Filed: Feb. 28, 2022

(65) Prior Publication Data

US 2022/0290207 A1 Sep. 15, 2022

Related U.S. Application Data

(63) Continuation of application No. 14/893,689, filed as application No. PCT/US2014/000137 on May 30, 2014, now Pat. No. 11,286,513.

(60) Provisional application No. 61/956,065, filed on May 31, 2013.

(51) Int. Cl.
| | | |
|---|---|---|
| C12Q 1/24 | (2006.01) | |
| B01L 3/00 | (2006.01) | |
| C12Q 1/04 | (2006.01) | |

(52) U.S. Cl.
CPC .............. *C12Q 1/24* (2013.01); *C12Q 1/04* (2013.01); *B01L 3/50825* (2013.01); *B01L 3/502753* (2013.01); *B01L 2200/0647* (2013.01); *B01L 2200/0684* (2013.01); *B01L 2200/10* (2013.01); *B01L 2200/141* (2013.01); *B01L 2300/023* (2013.01); *B01L 2300/044* (2013.01); *B01L 2300/0681* (2013.01)

(58) Field of Classification Search
USPC ...... 422/502–504, 68.1, 82.05, 402; 436/180
See application file for complete search history.

(56) References Cited

U.S. PATENT DOCUMENTS

| | | |
|---|---|---|
| 4,618,769 A | 10/1986 | Johnson et al. |
| 5,521,384 A | 5/1996 | Lynch |
| 6,379,920 B1 | 4/2002 | El-Sayed et al. |
| 6,414,311 B1 | 7/2002 | Wood et al. |
| 7,767,435 B2 | 8/2010 | Chiu |
| 8,735,822 B2 | 5/2014 | Thomson et al. |

(Continued)

FOREIGN PATENT DOCUMENTS

| | | |
|---|---|---|
| AN | 103055983 A | 4/2013 |
| WO | 2016063068 A2 | 4/2016 |

OTHER PUBLICATIONS

Adler, Belinda, et al. Optimizing nanovial outlet designs for improved solid-phase extraction in the integrated selective enrichment target—ISET, Electrophoresis 2012, 33, 3143-3150, 2012 Wiley-VCH Verlag GmbH & Co. KGaA, Weinheim, www.electrophoresis-journal.com.

(Continued)

*Primary Examiner* — Dean Kwak
(74) *Attorney, Agent, or Firm* — Edell, Shapiro & Finnan, LLC

(57) ABSTRACT

Devices and methods are provided to detect the presence of bacteria and small microorganisms, and to identify various microbial attributes rapidly.

20 Claims, 2 Drawing Sheets

Schematic of the components of the proposed device

Schematic of the proposed microfluidic separation stage

(56) References Cited

U.S. PATENT DOCUMENTS

| | | |
|---|---|---|
| 11,286,513 B2 * | 3/2022 | Krishnamurthy ........ C12Q 1/04 |
| 2002/0179445 A1 | 5/2002 | Alajoki et al. |
| 2003/0219713 A1 | 11/2003 | Valencia et al. |
| 2008/0003142 A1 | 1/2008 | Link et al. |
| 2010/0129857 A1 | 5/2010 | Walsh et al. |
| 2010/0203521 A1 | 8/2010 | Klapperich et al. |
| 2010/0216208 A1 | 8/2010 | Mueth et al. |
| 2012/0091235 A1 | 4/2012 | Li et al. |
| 2013/0037719 A1 | 2/2013 | Melling et al. |
| 2013/0085680 A1 | 4/2013 | Arlen et al. |
| 2015/0321191 A1 | 12/2015 | Kendall et al. |

OTHER PUBLICATIONS

Sufian F. Al-Khaldi, et al., Accelerating Bacterial Identification by Infrared Spectroscopy by Employing Microarray Deposition of Microorganisms, Foodborne Pathogens and Disease, vol. 1, No. 3, 2004.

K.L. Andrew Chan, et al., Rapid prototyping of microfluidic devices for integrating with FT-IR spectroscopic imaging, Jun. 7, 2010, National Library of Medicine, Lab Chip, 2010, 2170-2174, The Royal Society of Chemistry 2010, www.rsc.org/loc / Lab on a chip.

Jan Eijkel, Chip-based HPLC: the quest for perfect column, Jun. 7, 2010, National Library of Medicine, Lab Chip, 2007, 815-817 / 815, The Royal Society of Chemistry 2007, www.rsc.org/loc / Lab on a chip.

Yildirim Cinar, et al., Effect of hematocrit on Blook Pressure Via Hyper viscosity, American Journal of Hypertension, Ltd. Jul. 1999; vol. 12, No. 7, Published by Elsevier Science, Inc.

Fiorini, Gina S., et al., Disposable microfluidic devices: fabrication, function, and application, BioTechniques 38:429-446, Mar. 2005, University of Washington, Seattle, WA, USA.

Fiorini, Gina S., et al., Fabrication improvements for thermoset polyester (TPE) microfluidic devices, Advance Article on the web May 11, 2007, The Royal Society of Chemistry 2007, www.rsc.org/loc / Lab on a Chip.

T.M. Floyd, et al., A silicon microchip for infrared transmission kinetics studies of rapid homogeneous liquid reactions, MicroChemical Systems Technology Center, Department of Chemical Engineering, Microsystems Technology aboratory, Massachusetts Institute of Technoogy, Cambridge, MA.

Karolin Geyer et al., Microreactors as Tools for Synthetic Chemists—The Chemists' Round-Bottomed Flask of the 21st Century? 2006 Wiley-VCH Verlag GmbH & Co., KGaA, Weinheim, Chem. Euro. J. 2006, 12, 8434-8442.

D. Helm, et al., Classification and identification of bacteria by Fourier-transform infrared spectroscopy, Journal of General Microbiology (1991), 137, 69-79.

Rachel Herzig-Marx et al., Infrared Spectroscopy for Chemically Specific Sensing in Silicon-Based Microreactors, Anal. Chem. 2004, 76, 6476-6483, Department of Chemical Engineering and Microsystems Technology Laboratories, MIT.

Lotien Richard Huang, et al., Continuous Particle Separation Through Deterministic Lateral Displacement, Science 304, 987 (2004), DOI: 10.1126/science. 1094567, www.sciencemag.org, Science vol. 304, May 14, 2004.

David W. Inglis et al., Highly accurate deterministic lateral displacement device and its application to purification of fungal spores, Biomicrofluidics 4, 024109 (2010), 2010 American Institute of Physics.

David W. Inglis, et al., Critical particle size for fractionation by deterministic lateral displacement, Mar. 17, 2006, www.rsc.org/loc / Lab on a Chip.

Mossoba, M.M., et al., Application of a Novel Hydrophilic Infrared-Transparent Membrane to the Differentiation between Microcoloies of Enterobacter sakazakii and Klebsiella pheumoniae, Journal of Food Protection, vol. 70, No. 5, 2007, pp. 1241-1245.

William C. Patrick, III, et al., Continuous Centrifugation in Virus Processing, Journal of Biochemical and Microbiological Technology and Engineering, vol. II, No. 1, pp. 71-80 (1960).

Aaron M. Streets, et al., Chip in a lab: Microfluidics for next generation life science research, AIP Biomicrofluidics 7, 011302 (2013), http://dx.doi.org/10.1063/1.4789751.

Christopher C. Striemer, et al., Charge- and size-based separation of macromolecules using ultrathin silicon membranes, 2007 Nature Publishing Group, Nature, vol. 445, Feb. 15, 2007, p. 749-753.

Jiashu Sun, et al., Double spiral microchannel for label-free tumor cell separation and enrichment, www.rsc.org/loc; Lab Chip, 2012, 12, 3952-3960.

Junya Takagi et al., Continuous particle separation in a microchannel having asymmetrically arranged multiple branches, www.rsc.org/loc; lab on a chip, May 19, 2005.

Masumi Yamada et al., Microfluidic Particle Sorter Employing Flow Splitting and Recombining, Dept. of Chem. & Biotech., School of Engineering, UofTokyo, Anal. Chem. 2006, 78, 1357-1362.

Kerwin Kwek Zeming, et al., Rotational separation of non-spherical bioparticles using I-shaped pillar arrays in a microfluidic device, Mar. 27, 2013, www. nature.com/naturecommunciations.

European Search Report Application No. 14803403.6-1405, dated Jan. 2, 2017.

Frank Bokeloh, Master Thesis Design and Fabrication of Microfluidic Platform for Raman Spectroscopy Based Cell Diagnostics, http://www.dcu.ie/ducreeje/Reprints/Bokeloh113masters.pdf, Apr. 15, 2013, pp. 1-89.

Garip Sebnem, The Characterization of Bacteria with Fourier Transform Infrared (FTIR) Spectroscopy, http://citeseerx.ist.psu.edu/viewdoc/download?doi=10.1.1.632.7642&rep=rep1&type=pdf, Graduate School of Natural and Applied Sciences of Middle East Technical University, Jan. 1, 2005, pp. 1-99.

R.J. Davis et al., Fourier Transform Infrared (FT-IR) Spectroscopy: A Rapid Tool for Detection and Analysis of Foodborne Pathogenic Bactieria, Microbial Biotechnology vol. II, Jan. 1, 2010, pp. 1582-1584, https://www.researchgate.net/profile/Reeta_Davis/publication/257781807_Fourier_Transform_Infrared_FT-IR_Spectroscopy_A_Rapid_Tool_for_Detection_and_Analysis_of_Foodborne_Pathogenic_Bacteria/links/5614e8f108ae4ce3cc649412.pdf.

Sarah Pegram, All Graduate Theses and Dissertations Graduate Studies Use of Fourier Transform Infrared Spectroscopy for the Identification of Bacteria of Importance to the Food Industry, Jan. 1, 2007, http://digitalcommons.usu.edu/cgi/viewcontent.cgi?article=1072&context=etd*abstract.

Kerwin Kwek Zeming et al., Rotational separation of non-spherical bioparticles using I-shaped pillar arrays in a microfluidic device, Nature Communications, vol. 4, Mar. 27, 2013, p. 1625.

Mohamed Al-Fandi et al., New design for the separation of microorganisms using microfluidic deterministic lateral displacement, Robotics and Computer Integrated Manufacturing, vol. 27, No. 2, Apr. 1, 2011, pp. 237-244.

Tian, W et al., Microfluidics For Biological Applications. New York; Springer Science + Business Media. 2008, a-ISBN: 978-0-387-09480-9, p. 47.

Alvarez-Ordonez, A et al., Fourier Transform Infrared Spectroscopy As A Tool To Characterize Molecular Composition And Stress Response In Foodborne Pathogenic Bacteria. Journal of Microbiological Methods, Mar. 2011, vol. 84, No. 3; pp. 369-378.

PCT Search Report for PCT/US14/00137 dated Aug. 28, 2014.

Zelenin, Sergey et al., Bacteria Isolation from Whole Blood For Sepsis Diagnostics, 15th International Conference on Miniaturized Systems for Chemistry and Life Sciences, Jan. 1, 2011, pp. 518-520.

Hansson, Jonas, Microfluidic blood sample preparation for rapid sepsis diagnostics, Jan. 1, 2012, XP055594823, ISBN: 978-91-7-501428-9, 52 pages.

Extended European Search Report from the European Patent Office for European Patent Application No. 19168711.0, dated Jun. 21, 2019, 9 pages.

(56) References Cited

OTHER PUBLICATIONS

Sun et al., Double spiral microchannel for label-free tumor cell separation and enrichment, Lab Chip, 2012, 12, 3952-3960 (year: 2012).

* cited by examiner

Figure 1. Schematic of the components of the proposed device
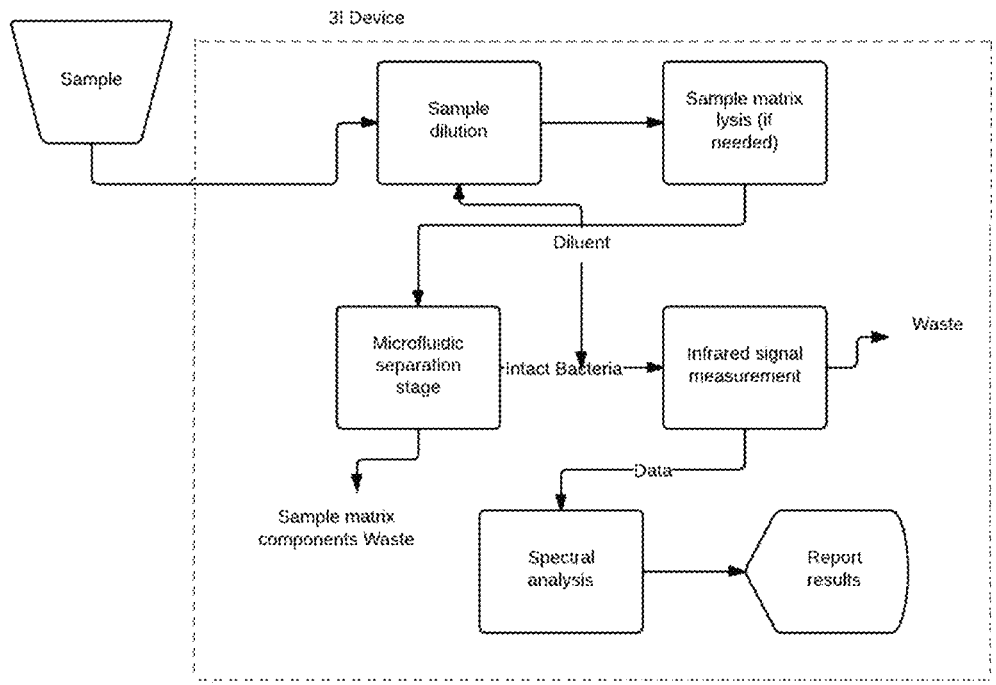
Figure 2. A representative FT-IR absorbance spectrum of a gramm-negative bacterium Salmonella enterica
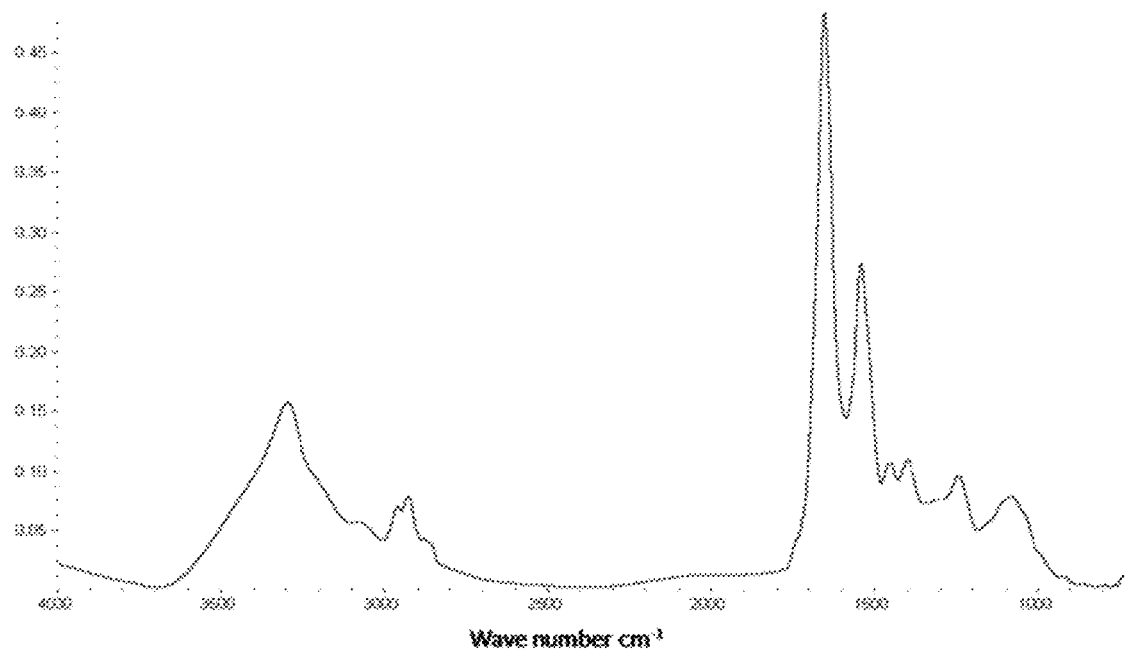

Figure 3. Schematic of the proposed microfluidic separation stage
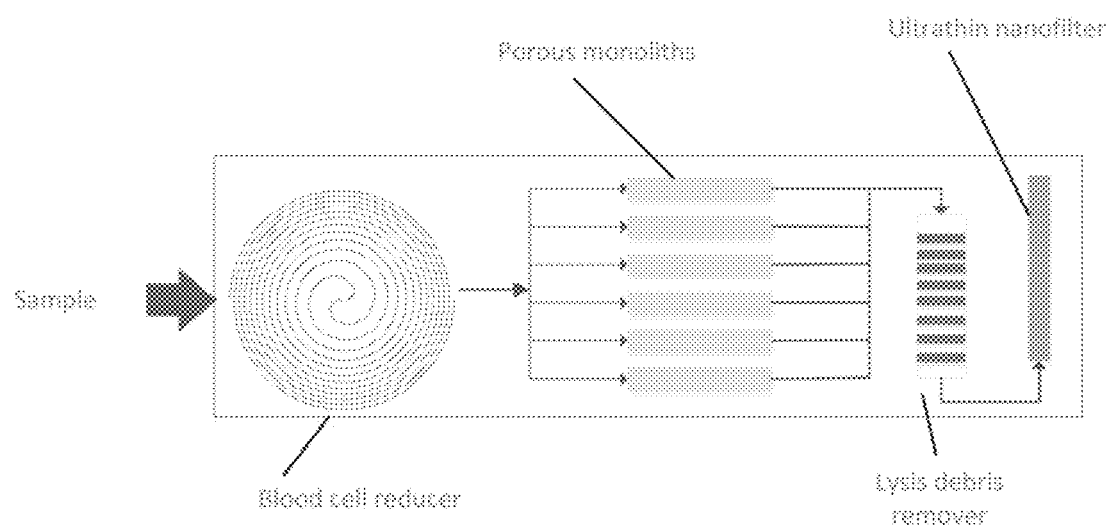

RAPID MICROBIAL DETECTION

CROSS REFERENCE TO RELATED APPLICATION

This application is a continuation of U.S. patent application Ser. No. 14/893,689 filed Nov. 24, 2015, titled "Rapid Microbial Detection," which is a national stage application of International Patent Application No. PCT/US2014/000137 filed May 30, 2014, titled "Rapid Microbial Detection," which claims priority to U.S. provisional patent application Ser. No. 61/956,065, filed May 31, 2013, titled "Rapid Microbial Detection," the entirety of all of which is incorporated herein by reference.

TECHNICAL FIELD

The present invention relates to devices and methods to detect the presence of microorganisms, such as bacteria, and to identify various microbial attributes rapidly.

BACKGROUND

Each year more than 2 million children around the world under the age of five die from bacterial pneumonia alone. In addition, foodborne and waterborne diseases (normally involving bacteria) kill about 2.2 million people globally, generally in regions where analytical devices are unavailable. Thus, microorganism detection technologies that are portable and deployable would provide tremendous health benefits worldwide.

Current methods to detect microorganisms normally require more than one day to provide results. The traditional culture-based method takes even longer (1-7 days) and is frequently used on account of its low cost and greater sensitivity. As a result, various treatment decisions involving patients are delayed until availability of results. In locations without access to a well-equipped laboratory that can perform sample culturing, the sample has to be shipped, thereby adding delay, cost, and logistic issues.

Because of the delays and costs involved, treatment decisions are initially based on "educated guesses" followed by a more specific decision based on the laboratory results or empirical results with a particular medication. For instance, a physician may prescribe a broad-spectrum antibiotic to cover a wide variety of bacteria without knowing if the infection is bacterial. If the presence of bacteria is confirmed and if the identity of the bacteria is determined, then the antibiotic is changed to one that is more appropriate for those bacteria. A patient's response is also a factor in selecting an optimal treatment.

More rapid analyses are critical in the treatment of bacterial infections since morbidity and mortality have been directly correlated to the early initiation of appropriate antibiotic therapy.

Similarly, in the case of food manufacturing, food may be shipped without waiting for the results due to their perishable nature. If the presence of bacteria is confirmed in the sample, then the food is recalled. At times, a customer may have consumed the food before these results are available. This is one of the major causes for various food contamination outbreaks. In the U.S. alone, it is estimated that there are 9.4 million episodes of foodborne illnesses resulting in 1,300 deaths per year and direct healthcare costs of treating people of approximately $152 billion a year. And companies lose hundreds of millions of dollars due to costs of recall, rejected batches, compensation, market share, and loss of reputation. Additionally, due to globalization and sourcing of raw materials from all over the world, a raw material may be used in a process before ascertaining the presence of bacteria. If harmful bacteria are found to be present in the raw material, this may result in the rejection of a processed batch causing substantial financial harm to the manufacturer. Thus, rapid and portable detection technologies would provide tremendous health as well as economic benefits worldwide.

Most of the current rapid methods rely on bacterial identification based on antibody recognition or specific nucleic acid sequence binding. While these methods offer an increase in speed (compared to traditional culture) and specificity of detection, they are more expensive compared to the traditional culture methods and may not be as accurate. Further, while in principle almost all species can be identified on the basis of their specific nucleic acid sequence, practical limits on multiplexing mean that these techniques can identify only a few microorganisms at a time. As a result they are not an effective screening technique where the pathogen may be one of a large number of possible pathogens. Other techniques such as mass spectrometry based identification may offer lower cost per test but require highly skilled operators and very expensive equipment in a specially equipped laboratory. As a result, many small to mid-sized organizations and businesses, including hospitals and agricultural processing plants, tend to use traditional culture method despite the longer time to diagnosis.

Clearly, there is a need for methods and devices that can be used to identify microorganisms at the point of need (for example, a patient's bedside, manufacturing site, farm, etc.) and that provide rapid and accurate results at a relatively low cost.

SUMMARY

The present invention provides a rapid and integrated detection and identification system for various bacteria and other unicellular and multicellular microorganisms. It requires relatively small amounts of sample and processes samples and identifies microorganisms without culturing and without manual intervention steps typically found in devices used in the field. The detection and identification system operates rapidly compared to previously known devices, providing results in about one hour or less. Portable devices embodying the detection and identification system are contemplated for use in the field in a wide variety of locations and environments. As used herein, the term "bacteria" is used for convenience rather than reciting each time "bacteria and/or other small microorganisms" unless it is clear from the context that only bacteria or some other microorganism is being discussed.

Devices and related methods according to the present invention generally comprise a microfluidic separation stage or component and an infrared (IR) spectrometric stage. An identification stage preferably is also part of the detection system. Preferably, the identification stage further includes both a spectral analysis stage and a result reporting stage. The identification of microorganisms in the sample is performed at the point-of-use or remotely, and the data generated for the identification of microorganisms in the sample may be stored and analyzed locally or output for remote analysis or storage.

A preferred embodiment of the detection systems and devices according to the present invention is applicable to the analysis of bacteria in bodily fluids such as blood, and is configured to lyse blood cells in blood samples and remove detritus and other debris that might interfere with detection and identification. Components of the system generally provide the capability to preferentially select and to concentrate the cells of interest (for example, bacteria, fungi, yeast, which may be spherical, non-spherical, or deformable). Thus, in other embodiments, the detection system identifies microorganisms such as fungi, and small unicellular and multicellular organisms.

The detection system processes and detects and identifies microorganisms in liquid samples such as whole blood, plasma, serum, saliva, urine, cerebrospinal fluid, water, and fruit and vegetable juices. The volume of such samples is relatively low compared to previously known devices, and preferably ranges from about 0.1 mL to about 10 mL. The ability to process larger sample volumes of about 1-10 mL aids in the detection and identification by increasing the probability of the microorganism contaminant in the sample and its amount. Most current diagnostic systems utilize lower volumes of sample (less than about 0.5 mL). The detection system also processes other types of samples such as meat, produce, processed food, dairy products, poultry products, pharmaceutical process streams, bulk drug substance, and final drug product.

The microfluidic separation stage preferentially selects intact microorganisms. It also selectively lyses non-microbial cells. Notably, the microorganisms in the sample do not need to be cultured or otherwise isolated from the sample prior to application of the sample to the detection system prior to analysis.

The microfluidic separation stage optimally contains a measurement preparation stage to concentrate the intact bacteria and then to direct or channel them to an IR-compatible surface. Optimally, the microorganisms in the sample to be analyzed are concentrated to facilitate detection and analysis by reducing the sample's volume or by filtration. And, notably, the detection system according to the present invention separates out and removes the debris from the lysis of non-microbial cells without using nucleotides (such as DNA), antibodies, or other ligands and reagents that specifically recognize and bind the microorganisms of interest, such as bacteria.

In another preferred embodiment, the infrared spectrometric stage utilizes beam condensers to reduce the width of the IR beam to which the microorganisms in the sample are exposed. Preferably, the IR spectrometric stage also contains a single-point or a focal plan array detector.

Preferably, a measurement stage is provided to measure the IR signatures of the microorganisms in transmission mode. In another of its aspects, the measurement is performed using other modes commonly used in infrared spectroscopy such as attenuated total reflection (ATR), and diffuse reflection infrared Fourier transform (DRIFT).

In preferred embodiments, the measurement stage includes ultrathin polycrystalline silicon filter. In other embodiments, the measurement stage may include a flow cell or detection window.

Other embodiments of the present invention also include a waste collection stage. Preferably, a computer system or microprocessor are included in the detection system to collect, digitize and process the acquired data. Embodiments including a reporting stage to provide output of analyzed data are preferred. Preferably, the detection system also includes a control stage.

The identification stage of the present invention preferably utilizes standard chemometric approaches to compare sample IR spectra against those in a reference database in order to identify the genus, species, or strain of bacteria and other microorganisms detected and analyzed. In specific use situations, reference spectra in the database would include IR spectra of particular predetermined microorganisms whose detection and identification are desired in an emergency or acute setting. It is contemplated that a neural network or other computational approaches may be used to identify the bacteria and other microorganisms in a sample.

In yet another aspect of the present invention, a microfluidic separation device is provided. The device preferably includes a first separation stage to separate debris and smaller analytes and contaminants from intact microbial cells, a lysis stage to selectively lyse non-microbial cells, and a second separation stage to separate lysed cells and cellular debris from the microbial. The first separation stage is particularly useful for the analysis of microorganisms present in a blood sample. If the sample matrix is cerebrospinal fluid or an environmental sample, such as pond water for example, then the first separation stage may be unnecessary as would readily be determined by a person skilled in the art. The second separation stage optionally may operate by filtration or other methods known to persons skilled in the art.

Another aspect of the present invention relates to a method of detecting or identifying microorganisms in a sample by introducing the sample for processing into a detection system as described above, processing the sample and then obtaining the analyzed data output from the detection system. Contemplated microorganisms to be detected and/or analyzed in such methods include prokaryotes, eukaryotes, protozoans, filamentous fungi, and algae. The detection system is also intended to distinguish different species and strains of a specific genus, for instance different bacterial species from the genera *Staphylococcus, Escherichia, Listeria, Salmonella, Streptococcus, Klebsiella* and *Campylobacter.*

DESCRIPTION OF THE DRAWINGS

The following figures, which are described below and which are incorporated in and constitute a part of the specification, illustrate exemplary embodiments according to the disclosure and are not to be considered limiting of the scope of the invention, for the invention may admit to other equally effective embodiments. The figures are not necessarily to scale, and certain features and certain views of the figures may be shown exaggerated in scale or in schematic in the interest of clarity and conciseness.

FIG. 1 is a schematic showing the major components of the integrated detection and identification system and their functions.

FIG. 2 is an example of a plot of infrared absorbance versus wavelength for a particular species of bacteria.

FIG. 3 is a schematic showing another embodiment of the integrated detection and identification system.

DETAILED DESCRIPTION

There are several highly important features desired in rapid bacterial diagnostics—speed to result, the ability to identify a broad range of pathogens accurately, and simple/inexpensive operation. Historically, diagnosis of bacteria has relied on growth-based technologies in order to expand the population of bacteria to detectable levels. Most of the rapid diagnostic approaches used to-date have focused on reducing the time-to-result (TTR) post-culturing and/or through the use of proprietary media, which accelerate the growth of selected bacterial species. The reductions in TTR therefore have largely been incremental since the time needed for the bacteria to grow is the rate-limiting step.

Infrared and Raman spectroscopy have been widely studied and used for detection of various analytes, including bacteria. The spectroscopy relies on the unique patterns generated by the vibrational energies of the bonds that exist between atoms (for example, C—O, C—H, etc.). Helm et al. [1]

In the above studies, the identification of bacteria using Fourier transform infrared spectroscopy (FTIR) has been performed on cultured and isolated bacteria. Additionally, large quantities of bacteria (50-100 micrograms) are utilized in the analysis, which also uses complex procedures for instance, drying of bacteria on the surface of a reflective element to form a Biofilm. The analysis is performed in well-equipped laboratories involving highly skilled analysts and takes up to one week. El-Sayed et al. [2] report a method for analyzing three common bacteria in otitis media while submerged in a biologic fluid. The three most common bacteria studied were *Streptococcus penumoniae, Haemophilus influenza*, and *Morazella catarrhalis*.

In general, the present invention is useful in various applications and locations where rapidly determining the presence and identity of bacteria and other very small unicellular and multicellular organisms is of importance. These include, for example, medicine (to determine bacterial infections), food safety, pharmaceutical quality control (including biotechnology products), environmental monitoring, and biosurveillance. The invention thus enables, for example, detection and identification of bacteria rapidly, at low cost, and at the point of need permitting appropriate actions to be taken. These may include, for instance, rejecting a batch of food or pharmaceutical, subjecting the batch to additional treatment, or determining the course of treatment for a patient. The invention also relates to methods to detect the presence of bacteria and other very small unicellular and multicellular organisms, and to identify different attributes, for example, of bacteria, such as the species and strain, in any sample matrix using an integrated device.

In one preferred embodiment, the present invention offers the ability to use a portable and integrated device to detect all bacteria from any sample matrix (as long as the matrix is a liquid, suspension, gel, slurry, or is liquefied such as a solid that has been digested using enzymes or put through a blender with some liquid) without the need for culturing, using tagging or binding reagents such as antibodies or nucleic acid primers, requiring analysis at well-equipped laboratories, or requiring the services of highly skilled technicians.

The microfluidic separation component according to the invention is capable of separating intact bacteria (or other microorganisms) from the sample matrix, without a need for organism-specific reagents such as antibodies or nucleic acid probes. Preferred sample matrices are fluids such as water, whole blood, milk and juice. Other appropriate samples include plasma, serum, saliva, urine, cerebrospinal fluid, food (such as meat, produce, processed food, dairy products, and poultry products), pharmaceutical process streams, bulk drug substance, and final drug product.

The detection component according to the invention preferably is an infrared spectrometer that is capable of measuring the IR spectrum of intact bacteria (or other small organisms), for example, in a microchannel or filter.

For instance, in clinical use the diagnosis is achieved by placing a disposable microfluidic chip (FIG. 3) in the appropriate slot of a device according to the present invention, inserting a tube containing the clinical sample in the sample port, and initiating the analysis by pressing a start button. The identity of the bacteria will be displayed on an LCD screen on the instrument.

The results can also be communicated and stored in any of several digital and hard copy formats. The clinical sample (for example, blood) is prepared for infrared measurement by first separating blood cells from intact bacteria, then selectively lysing the non-bacterial cells, then separating the lysis debris from intact bacteria, and finally concentrating the intact bacteria on a small IR-compatible surface. The infrared spectra of the bacteria on the surface is measured using a spectrometer, which may be aided by beam condensers, objective lenses, and apertures. These spectra are then compared against those in a reference database to enable identification.

The invention relates, in part, to the discovery that bacteria in a sample can be concentrated sufficiently, for reliable identification by infrared spectroscopy, without culturing and that the infrared spectrum of a bacteria provides a unique fingerprint of the bacteria that aids in specifically identifying it. Furthermore, the embodiments described in this specification substantially minimize the need for handling and processing a sample compared with the purification and concentration techniques in conventional detection systems.

The above benefits arise from the unique sequence of unit operations and their integrations as described in this application. For instance, use of mechanical forces to lyse non-bacterial cells by itself would not lend itself towards simple sample preparation. However, by combining it with a separation step before and after, it enables simple and effectively reagentless sample preparation. Also, most methods focus on lysing bacteria in order access their DNA or other bacterial biomarkers. The operational steps therefore not only have to clean up non-bacterial components but also separate the targeted biomarker from other bacterial components.

By focusing on isolating intact bacteria, not only is the operation simplified, but also the intact bacteria can be concentrated to levels suitable for detection and identification easily without requiring culturing. While the microfluidic chip containing concentrated intact bacteria could be used with various measurements (for example, colony cultivation, mass spectrometry, PCR, etc.), the preferred embodiment uses a technique such as infrared spectroscopy. This ensures measurement in a few minutes, enables label-free identification, and provides the ability to identify multiple pathogens from a single measurement.

The preferred detection device is portable for use in the field. Identification routinely can be made in well less than one hour because the sample does not require culturing and related manual intervention steps, which is required for conventional identification devices. For example, where a conventional device might require 1-5 days to culture the sample, the system of the present invention might require only as much time as to process the sample volume using the microfluidic component. Similarly, the time to generate a result, for example, an identification of the bacterial component will generally be on the order of minutes rather than tens of minutes or of hours.

Preferred detection devices also include an identification module that provides reference spectra for the bacteria in a sample and can generate a local identification. Alternatively, IR spectral information may be processed at a central location and reference spectra may be utilized through the internet, telephone, radio or other data transmission technologies. The detection is expected to be capable of detecting about 10 colony forming units/mL or better. The false positive rates are expected to be less than about 5% with the accuracy of identification being greater about 90%, 95%, 98% and 99% or better. These false positive and accuracy rates are comparable to those of conventional devices without the effort, training, and time needed to generate a result using these devices. Examples of bacteria that can be detected using this device include members of the *Staphylococcus, Escherichia, Listeria, Salmonella, Streptococcus*, and *Campylobacter* genera.

In one embodiment, the invention provides an integrated device for detecting bacteria in various matrices, where the device comprises: (a) a microfluidic separation stage to separate bacteria from the rest of the sample matrix, thereby enriching their concentrations, (b) a measurement preparation stage to serve as the interface with the measurement stage (or to transfer the bacteria into an IR-compatible solvent) (c) a measurement stage that measures the infrared signature of the bacteria in transmission mode, including other measurement modes known to persons skilled in the art such as attenuated total reflection (ATR), diffuse reflection infrared Fourier transform (DRIFT), and other modes which consists of the spectrometer (source and detector), flow cell or detection window, interface to provide digitized data for analysis, and a waste collection stage, (d) a microprocessor or similar computer system to collect and digitize the acquired data, (e) an analysis stage which comprises software to perform background and sample assessment, background subtraction, deconvolution and other conventional techniques to determine attributes of the bacteria and a database (or access to a database) consisting of the spectra of bacteria reference material, (f) a reporting stage which enables transmission of results into the desired format for comparison with databases, permits onscreen display, text messaging, and transmission and sharing onto other peripheral devices such as a printer or hand-held device, and (g) a control stage that comprises software to controls the timing of the different steps, power requirements, and parameters required at each step and phase of the present invention (such as fluid speed, centripetal force generated, scan speed, data acquisition rate, etc.).

In another embodiment, the microfluidic separation stage comprises a disposable mini-centrifuge or a spiral path and a fluid flow control system (which is non-disposable). It is contemplated that the fluid flow control system may be a vacuum pump or actuators for active and passive flow control. It is also contemplated that the mini-centrifuge or a spiral path is capable of generating sufficient centripetal force to separate the components of the sample matrix from the bacteria such that the bacteria are maintained intact. And the bacteria and the matrix (separated from the bacteria) are moved by the fluid flow control system through all the other stages of a device according to the present invention.

In some embodiments, the mini-centrifuge or a spiral path further comprise a sub-system to lyse the components of the matrix. Other embodiments comprise a component and means to mix the stream(s) from the microfluidic separation stage with a carrier solvent.

Yet other embodiments comprise an interface with the measurement preparation stage that helps transfer fluid from the microfluidic separation stage to the measurement stage. Typically, the diameter of the channel in such an interface would be in the range of about 0.1× to 10× relative to the diameter of the channel in the microfluidic separation stage. The measurement preparation stage optionally comprises a filter with a molecular size cut-off of about 0.45 microns or smaller and may be made of silicon, silicon nitride, polyethylene, polyvinyldifluoride, or Teflon® or other compositions known to persons skilled in the art.

It is contemplated that a carrier solvent or solution, when utilized, will be infrared (IR) compatible such as formaldehyde, n-hexane, ethanol, acetone. And the carrier solvent may contain some water in the range from about 0 to 90% by volume.

In other embodiments, the measurement stage comprises an infrared source, beamsplitter, mirrors, beam condenser, objective, and detector. And it may further comprise a flow cell or a detection window to enable measurement. Preferably, the source is capable of emitting radiation in the range from about 300 to 5000 cm$-1$, and may deliver coherent or incoherent light. It also may utilize a frequency comb in situations where a coherent beam containing a continuum of frequencies over one or several octaves are needed. The spectrum and power of these pulses are optimized to improve signal-to-noise ratio and to enhance resolution. Applications utilizing such frequency combs include classical and ultra-high resolution near-field microscopies. The infrared beam may be focused with the help of lenses and objective so that the beam width optimally ranges from about 1 micron to about 1 mm, as is commonly done using an FTIR microscope accessory. Preferably, the beam width approximates the dimensions of the microorganism being analyzed, for example, bacteria.

In yet another embodiment, the detector is capable of detecting infrared absorbance in the range from about 300 to 5000 cm$-1$. In a preferred embodiment, the detector comprises an array from about 1×1 to about 256×256. Additionally, the detection window comprises a variable path length, and is made using IR-transparent material (such as silicon, calcium fluoride, potassium bromide, or zinc selenide).

Persons skilled in the art will understand that the measurement stage may comprise various accessories that permit measurement in transmission, attenuated total reflection, and other reflection modes. Additionally, the detector preferably is located between 0.1 to 10000 wavelengths. Detectors located within one wavelength can be used to monitor the evanescent waves enabling inspection of the sample with very high spatial and spectral resolution. This location of the detector would typically be utilized in near-field infrared microscopy applications. Detectors located further away represent the more classical approach to infrared spectroscopy.

Other preferred embodiments comprise an analysis stage that utilizes fourier or fast Fourier transforms to convert the acquired data to a spectral signature. The analysis stage further utilizes the signal from the fluid flowing through the detection window over time to identify the baseline signal or to determine changes to the initial signal. This signal may be, for example, at the frequency ranges where water, protein, peptidoglycan, or phospholipids absorb. Systems according to the invention will distinguish between the baseline signal and the sample signal, and are capable of subtracting the baseline signals from the sample signals. Preferably the analysis stage utilizes second derivatives and other techniques such as Gaussian deconvolution, autocorrelation, and Savitzky-Golay smoothing, which are well known to a person skilled in the art of analyzing and interpreting spectral data.

In another aspect of the invention, the analysis stage evaluates the spectral profile obtained from each sample signal to determine if it could potentially be from a bacteria and labels such profiles or signals within a profile as bacterial signals. And the system determines whether a detected bacterial signal is attributable to, for example, a gram positive, gram negative, or gram variable bacteria. In preferred embodiments, the analysis stage determines the confidence (probability) of the determination. In certain embodiments, the analysis stage compares the bacterial signals with spectra in a database to establish the identity of the bacteria.

In other preferred embodiments, the reporting stage transmits the result from the analysis stage to an output device of choice (for example, on a screen, printer, USB stick) or transmits it, for example, via Wi-Fi, wired, Bluetooth or cellular modes to the destination of choice.

In yet another aspect of the invention, the measurement stage comprises a waste collection receptacle that is sealed and will be disposed according to procedures determined by the user of the system. Optionally, the measurement stage comprises wash solvents and a wash step that washes the non-disposable surfaces that contacted the sample. The wash solvents may consist of a mixture of ethanol and water, water and detergent, and pure water may be used to reduce or prevent sample carryover from one measurement to the next. Optionally, the measurement stage may consist of the channel being overlaid on an accessory such as an ATR or a transmission cell or a channel consisting of pores (about 10 nm to 1000 nm), which would enable filtrate smaller than these pores to be separated from intact bacteria by filtration.

Briefly described, in a preferred embodiment, the present invention provides a means to detect and identify bacteria in any liquid sample matrix using a combination of microfluidic-based separation and spectrometry. The sample matrix in this embodiment is any matrix that contains bacteria.

The integrated device consists of a stage that separates the bacteria, for example, from the rest of the sample matrix and prepares it for the measurement stage, which obtains the infrared spectrum of the bacteria and the background. The spectra is analyzed to determine if characteristic features associated with a bacteria are present and whether the features provide additional features that permit classification of the bacteria, for example, as gram positive, gram negative, or gram variable, or on the basis of their genus, species, strain, or antibiotic resistance.

Preferably, Fourier transform infrared spectroscopy (FTIR) is utilized to detect and identify the bacteria but other spectroscopic techniques (for example, Raman spectroscopy or mass spectrometry) can be utilized as well. FTIR is a well-known analytical technique. The present invention enables microorganism identification and also diagnosis at the point of need and without a need for culturing a sample. It also enables disease diagnosis through identification of pathological bacteria at low cost without utilizing antibody or nucleic acid sequence based identification.

Using this method, any sample matrix can be analyzed for the presence and identity of the bacteria, if present, without the need for culturing. This dramatically reduces the time needed for analysis. By not using any antibody or nucleic acid primer for recognition, the device is low-cost, portable, and does not need additional laboratory infrastructure to support and enable its use at the point of need.

The present invention, in a preferred embodiment, is an integrated device that is capable of separating bacteria from a sample matrix, enriching the bacteria, obtaining the infrared spectrum of the background and the bacteria, subtracting the background spectrum from the bacteria spectrum, analyzing the resulting spectrum through known deconvolution techniques and reporting the results using peripheral devices that are appropriate for the particular intended analytical purpose. The analysis of the spectrum may also involve comparing the spectrum of bacteria to that of a reference, which is stored in a database, FIG. 1 provides a schematic that identifies the major components of the device according to the present invention, and identifies the major functions of these components. In general, a sample 101 is obtained for analysis. This sample is prepared by dilution or other steps as indicated by the sample dilution stage 103. Some of the components of the sample matrix 105 are lysed and intact bacteria are separated from the matrix components using a microfluidic separation stage.

Next, intact bacteria are provided to the infrared signal measurement stage 107. Data from this measurement are communicated to a spectral analysis unit 109. And results of the analysis are reported via reporting stage 111. The entire process is designed to be a continuous process without any interruptions to the separation and measurement or requiring any manual intervention.

All liquid flow is controlled and managed by micropumps or capillary action. The pump can use any of the commonly utilized driving forces for pumping fluid—piezoelectric, pneumatic, electroosmotic, etc. Following the treatment in the sample dilution stage 103, the entire sample is transferred to the sample matrix lysis stage 105 and the microfluidic separation stage 105. The movement from one stage to the other is continuous and not performed in batch mode. The separation of the intact bacteria occurs as the fluid (containing intact bacteria and components of the sample matrix) moves through the microfluidic separation stage resulting in two outlet streams (shown in FIG. 1). The sample component stream is collected in a waste receptacle and is normally discarded while the stream containing intact bacteria moves to the measurement stage 107.

The fluid containing largely intact bacteria moves through the measurement stage where the IR signal is measured and produces a quantified digital signal. The fluid is collected in a waste receptacle, which is discarded. In certain applications, the analyte of interest (for example, cholesterol, glucose, etc.) may be present in the waste stream from the measurement or separation stage. In such situations, the waste stream may also be routed to the measurement stage to measure these analytes utilizing the same detection apparatus (FTIR).

The digitized data from the measurement stage is then transmitted to the spectral analysis stage 109. The transmission can be internal to the device, to a local computer or server and can be accomplished using wires (for example, an RS232 connection) or wireless (Bluetooth or Wi-Fi).

Following analysis of the digitized data (as described in the spectral analysis stage 109), the results are transmitted to the same or other appropriate peripheral device 111, again using a wired or a wireless connection, as needed.

Stages 103 & 105 are disposable and are discarded following analysis of each sample. The stages can handle either a single sample at a time or multiple samples simultaneously. In the latter case, multiple channels are utilized to move the fluid until the measurement stage. At this stage however, the different channels are opened based on a timing sequence controlled by a conventional microprocessor so that the IR spectrum of one sample at a time is measured. All of the streams go to the same waste receptacle in the end.

Sample Matrix 101:

The sample itself can be whole blood, or a food matrix as described. In the case of solid samples, a preparatory stage involving "liquefying" the solid sample, such as food, is needed. This can be accomplished using practices that are well known and practiced by food safety testers. They typically involve blending or mixing in a Waring® blender or a Stomacher® blender, such as the Stomacher® 400, and the Stomacher® 3500.

Any container that is capable of holding liquids can be used as a sample container/receptacle such as test tube, microcentrifuge tube, or a simple plastic container. The container is normally glass or polypropylene though any biocompatible material that does not adsorb bacteria or the analyte of interest (such as other organisms, cholesterol, glucose, urea, etc.) can be used. The container size depends on the nature and volume of the sample and can range from 10 uL to 500 mL. The requirements of the container used are that: (i) it should be capable of being sealed (to prevent contamination) and (ii) it should have an outlet port that is compatible with the sample dilution stage 103. In its preferred embodiment, the sample container is a venous blood collection tube such as, for example, a Vacutainer® tube. These typically and preferably consist of a test tube with a tube top that can be pierced and may contain agents such as EDTA to prevent blood clotting.

The tube top is placed against the first stage (Sample Dilution Stage 103) that contains a needle to pierce the tube top. The needle may be made of stainless steel or other similar materials. In the case of other containers, an outlet from the sample container that forms a tight seal with the sample dilution stage is needed. This connector can be made of polypropylene, polyvinyldifluoride, silicone, Teflon®, or any biocompatible material that does not adsorb bacteria or the analyte of interest. The diameter of the connector can be varied depending on the volume of the sample. In its preferred form, the diameter is greater than about 1 cm. Though smaller diameters can be used, the diameter cannot be smaller than 200 microns. The length can be varied depending on the conditions of the measurement. A key requirement is that the hold-up volume in the connector tube should be approximately one-tenth the sample volume or less.

A fluid control device (such as a micropump) preferably will be used to move the sample through the different stages. This can be positioned either beside the sample receptacle (preferred) so that it pushes the liquid through the intended flow path or beside the waste receptacle so that it pulls the liquid through the intended flow path.

Gravity may be used to assist the fluid flow and prevent air bubbles from entering the fluid flow path. To achieve this the sample receptacle may be placed at a higher elevation relative to the next stage.

Sample Dilution Stage 103:

The sample enters this stage via the connector/needle. From this point until the waste receptacle, the system is sealed to prevent/reduce chances of external contamination. A one-way vent optionally may be provided to ensure that a vacuum does not form within the system. In addition, a degasser component optionally may be added to ensure a smooth flow.

Sample components refer to different elements of the matrix depending on the sample. For example, in the case of identifying the bacteria present in blood, the sample components include red blood cells, white blood cells, plasma proteins, platelets, and other blood factors. In the case of food, the components include elements that constitute particles of food or its constituents (such as fatty acids, fats, lipids, proteins, etc.).

In this stage the sample is diluted to ensure that the viscosity of the fluid is similar to that of water and filtered to exclude very large components in the sample matrix.

A diluent preferably water (but which can also be phosphate buffered saline or other biologically acceptable buffer) is utilized for dilution. The volume of diluent added is to ensure that the viscosity is reduced to be similar to that of water (1 centipoise). For example, the typical viscosity of blood is approximately 10 centipoise at 20° C. The high viscosity of blood is largely due to the presence of hematocrit and the relationship between hematocrit and viscosity is well known. [3] Diluting blood in the range of about 5 to 50-fold (preferred target is about 10-fold) will reduce the viscosity to the desired level ensuring that the flow of the sample through the system is not affected due to increased viscosity.

The diluent is typically stored in a bottle or bag made of glass or plastic (polyethylene) with a seal that can be pierced or with an outlet tube. The bottle, in its preferred form, is stored inverted and the diluent is added to the stage via the needle/connector. The material of construction and considerations are similar to those described for the sample receptacle. The addition of the diluent may occur due to gravity (preferred) or via a fluid control device. Optionally, a device according to the present invention may include a hook or other element to hold a fluid reservoir. Optionally, the sample is filtered following dilution.

A sequence of filters with varying pore sizes may be used to prevent clogging downstream. These filters will all possess a pore size greater than the size of the bacteria (generally 2-10 microns) when bacteria are the intended organism or analyte to be identified, but are preferably greater than about 100 microns, which should permit passage of the analytes and restrict matrix material. The filters can be constructed of commonly used materials such as polyethylene, polyvinyldifluoride, or Teflon®, though other materials may also be considered as will be known to persons skilled in the art. The diameter of the filter can vary from 1 cm to 15 cm. Large volumes of sample (for example, greater than about 25 mL) will require a larger diameter filter. The size of the filter can be determined by one of the three traditional methods used to size filters—Volume endpoint (Vmax), Pressure endpoint (Pmax), and turbidity endpoint (Tmax). The preferred method is the Vmax method. The sample flow direction can be tangential to the filter surface or longitudinal to the filter surface. The former is the preferred embodiment to reduce the chances of filter clogging due to the components of the sample matrix.

Fluid flow to the next stage occurs via a manifold (preferred embodiment). While a connector of short length (less than about 10 cm) could be utilized, a tightly sealed manifold connecting the two stages is preferred. The diameter of the manifold optimally will range from about 100 microns to about 10 cm. The manifold, in its preferred form, is made from a thermosetting plastic that is analyte-compatible (that is does not adsorb or interact significantly with the analyte, such as bacteria).

Microfluidic Separation Stage 105:

The separation stage is a disposable component that is intended to be single-use. The separation stage can accommodate analysis of a single sample or multiple samples. A number of methods and approaches are known and utilized for making microfluidic devices such as [4-6]. The separation stage consists of two sections—a sample lysis 105A section and a separation section 105B. While the presence of the lysis section is optional, the preferred embodiment includes both sections. The purpose of the separation stage is to isolate and concentrate intact bacteria for infrared analysis.

FIG. 3 shows the schematic of the preferred embodiment of the separation stage 105. In the preferred embodiment, large non-bacterial cells (such as red blood cells) are first separated from intact bacteria using inertial focusing. This is followed by selective lysis of the remaining non-bacterial cells (in the preferred embodiment, by the use of porous monoliths) resulting in fluid containing intact bacteria and non-bacterial cell debris. The debris is then separated from intact bacteria using differences in hydrodynamic size. In the preferred embodiment, this is achieved by deterministic lateral displacement. This stage also reduces the total volume of the fluid that moves to the filtration stage. In the preferred embodiment, the intact bacteria is readied for infrared analysis by filtering the fluid using ultrathin silicon membrane filters, which eliminates water and any remaining lysis debris leaving intact bacteria on the surface of the filter, which can be analyzed by any appropriate technique. In the preferred embodiment, this technique is infrared spectroscopy. The entire separation and concentration is accomplished without the use of reagents such as DNA sequences or antibodies.

The separation stage can be connected to the stages preceding (103) and following (107) using connectors or manifolds (preferred). These can be fabricated using any thermoplastic material that is compatible with the analyte or glass. The preferred materials of construction are polycarbonate and cyclic olefins. Examples of the choice of materials and methods for forming the manifolds and connectors have been described in the literature, for example [7]. The inner diameter of these tubing can be in the range of about 0.001 mm to about 10 mm with a length ranging from about 0.1 mm (manifold) to about 1 m. A shorter length is always preferred.

Lysis Section 105A:

Following filtration and before reaching the separation stage, another procedure, as discussed below, is applied to disrupt non-bacterial cells. This is likely to be needed when dealing with whole blood, which contains red blood cells, white blood cells, and platelets.

The disruption of the non-bacterial cells can occur through mechanical means (preferred) relying on shear stress to lyse the cells or by chemical means. For disruption by shear stress, a sample is typically forced through microporous surfaces that contain pores with a diameter of about 1-10 microns (for instance resins used in chromatography). The movement of cells such as white blood cells, red blood cells, and platelets through these pores creates a high shear force, which in turn, causes these cells to be lysed. However, bacterial lysis to a significant degree will not occur due to the more robust nature of the bacterial cell. Alternatively, chemicals such as polysorbates, triton X-100, sodium cholate, or tri(n-butyl)phosphate, may be used to disrupt cell walls by chemical means.

In the preferred embodiment, the lysis section 105A consists of microchannels packed with resins of the desired pore size and the sample is forced through these pores at a flow rate ranging from about 20 microliters per minute to up to 1 milliliter per minute (preferred is about 0.5 milliliter per minute). The channel width, height, and length are greater than about 100 microns, about 50 microns, and about 5 mm respectively. While a straight channel with the above dimensions is preferred, curved channels or channels that double back among themselves (to increase length of the channel without increasing the overall length of the stage) can also be utilized.

The materials of construction and fabrication of the channels are similar to those utilized for the separation section 105B described below.

In cases with a large load of non-bacterial components that are of similar sizes bacteria (for example, blood), an additional step prior to the lysis step may be added. The function of this step is to reduce the non-bacterial cells load prior to lysis in order to improve lysis efficiency and reduce the potential for clogging. Reduction of blood cells in the samples will be accomplished using inertial focusing taking advantage of the size difference between bacteria (1-5 μm) and red/white blood cells (7-15 μm). Of the various inertial focusing approaches, the use of spiral microchannels has been demonstrated as a uniquely efficient method to separate cells that are similar in size with high throughput and separation efficiency. [8] Spiral channels fabricated using thermoplastics will selectively reduce the concentration of non-bacterial cells such as red/white blood cells. The design and fabrication of the spiral channels are similar to those described in Separation Section 105B (Spiral path embodiment).

Fluid exiting the lysis stage is now a largely aqueous system, which consists of intact bacteria and multiple components, such as proteins, nucleic acids, fragments of cell walls and cell organelles. These fragments are typically smaller in size than the intact bacteria. This stage minimizes or eliminates non-bacterial components that are larger than the bacteria with an efficiency greater than about 80%. The same continuous channel without any resin serves as the inlet channel for the separation section 105B.

Separation Section 105B:

A preferred configuration for the separation section 105B is to flow a sample via a microchannel that traces a spiral path ("Spiral path" embodiment described below). Separation may also be achieved using deterministic lateral displacement (DLD), [9], [10] in which a linear array of microposts will serve to focus and direct larger rigid bacteria particles to an outlet channel while shunting smaller and flexible cell debris to a waste outlet. This separation method will also provide the added advantage of significantly reducing the total collected fluid volume. While the this section can be constructed using many different materials, the preferred material is a thermoset plastic, which can be easily fabricated at low cost and is generally compatible with food and biological matrices. The channels (spiral path, described below) can be manufactured using molding, photolithography, or micro-machining methods as are well known to those skilled in the art of microfluidic device fabrication. Any of these approaches can be adapted for producing the separation section described in this invention.

While microfluidic devices have reduced the volume of reagent needed and increased the speed of the analysis, they are usually able to handle only small volumes of sample. Thus, if the concentration of the analyte (for example, bacteria) is low, the signal from the analyte may be too low to be detected reliably, let alone used for identification. One way to improve the concentration has been to use a technique like PCR to amplify the analyte (nucleic acid) or to immobilize antibodies in order to concentrate the analyte.

In the present invention, by way of contrast, the separation and concentration is accomplished using physical forces, for example, inertial or centrifugal forces. Thus, there are no zones where the analyte has to contact a reagent in order to enable concentration or detection and relatively faster flow rates can therefore be utilized. This approach also enables processing of a large volume of sample which, in turn, decreases the lower limit of detection compared to other microfluidic devices.

The objective of the separation section to separate intact bacteria from the rest of the sample matrix and enrich it. The section relies largely on inertial/centrifugal forces to accomplish this task.

The inertial/centrifugal force can be generated by forcing the liquid through channels that describe a spiral fluid path, DLD, as discussed below in a preferred embodiment, or by a mini-centrifuge. The spiral microchannels & DLD microposts are fabricated on a microfluidic chip.

The magnitude of centripetal force or acceleration is related to the mass of the different components of the sample matrix. Thus, components that are smaller in mass compared to the bacteria will experience a smaller force relative to the bacteria.

The fluid flow is introduced to the spiral using the outer arm of the spiral (preferred embodiment). Alternatively, the fluid can also be introduced at the center of the spiral. If a mini-centrifuge is used, the fluid is normally introduced at the bottom of the centrifuge.

The Spiral Path Embodiment:

The path preferably is fabricated on a glass, PDMS, cyclic olefins, polycarbonate, or similar surface that has been used for preparing microfluidic chips. The process for fabricating such a path may be a lithographic technique. However, other processes are well known, understood, and utilized in the fabrication of microfluidic devices, as described before, and can also be employed.

The spiral may be a two-dimensional or three-dimensional spiral and can be any of the different types of spirals that have been mathematically defined (such as Archimedes spiral, Fermat Spiral, logarithmic spiral, etc.). A preferred spiral path is the Archimedes spiral.

The parameters of the spiral (usually radius and angle) can be further optimized to improve the efficiency of the separation as can routinely be accomplished by persons skilled in the art.

The fluid entering the spiral path is preferably discharged into the outlet (where the bacteria are being directed) or a discharge channel (to collect the sample matrix components).

The outer edge of the channel optimally will have openings that lead to a separate discharge channel. The openings can be rectangular, circular or any shape with an effective diameter range from about 10 microns to about 250 microns. The channel too can be of any shape (rectangular is preferred) with a width greater than about 50 microns and a height between about 10 to about 500 microns.

The sample from the lysis section 105A enters the separation section at the outer arm of the spiral with a fixed velocity. The spiral shape of the flow channel causes the components that possess a lower mass than the bacteria to be directed to the discharge channel while the bacteria stay in the spiral fluid path until it they reach the exit of the spiral.

At the time of exit, the bacteria have largely been separated from most, if not all, of the other sample components. A reduction in the level of the sample components of greater than about 80% is achieved. The bacteria are in a largely aqueous medium.

This section has an interface that enables it to be locked in place against the measurement stage enabling a continuous fluid flow path between the separation and measurement stages as well synchronization of the steps (sequence and timing) taking place in the two stages.

Deterministic Lateral Displacement (DLD):

DLD uses flow through an organized array of "obstacles" (microposts) to separate particles based on their hydrodynamic size. It does this by selectively influencing the trajectory of particles above a certain size. The fundamental principles explaining this phenomenon have been known for close to a decade and have been modeled by several research groups [11-13]. These devices can be fabricated using standard lithographic techniques. Typical materials used to fabricate DLD devices include silicon and PDMS. The array of microposts can also be directly embossed onto thermoplastic devices.

The key variables that influence the separation include the size of the microposts, gap between microposts, and offset between two rows of the array (sometimes referred to as tilt angle relative to the fluid direction). In the preferred embodiment, the diameter of the cylindrical microposts may range from about 10-500 microns, the gap between the microposts can range from about 1-200 microns, and the offset can range from about 0.1 to 5 microns. The total length of the array ranges from 3 mm to 20 cm. Multiple arrays may be arranged in sequence to provide high resolution separation of the bacteria from the lysis debris. Other geometries for the micropost, such as I-shape, can also be used to accomplish the separation as described by Zeming et al. [14]

The inlet to the DLD is the same as the outlet from the previous stage. An additional input that permits addition of carrier solvent (such as water) may also be utilized. The design of the DLD ensures that the intact bacteria are pushed away from the main fluid stream (which carries the lysis debris). This "side stream" carrying the intact bacteria is the outlet that is directed to the next stage (infrared signal measurement stage 107). The main stream containing the lysis debris in the preferred embodiment is discarded. But this stream may also be utilized for further analysis. Reduction in lysis debris levels greater than about 95% is expected. The volume of the bacteria-containing stream is expected to be approximately one-hundredth of the initial volume entering this stage.

The use of DLD to separate RBCs from whole blood has been reported, for example by Zeming.[14] However, their application of DLD is effective because the size difference is large between RBCs and other blood cells. When it comes to separating bacteria from RBCs, white blood cells (WBCs), and platelets, the size differences are not as large. Inefficient separation of bacteria from other cells will increase the uncertainty in identification accuracy. This is because these other cells would contribute infrared signals of their own, if present, thus interfering with accurate identification.

The present invention optionally includes a selective lysis step, which has been found to provide a major advantage in the rapid detection of microorganisms, because it now "creates" a large size difference by lysing all cells other than bacterial cells. Following lysis of the blood cells, when applicable to a particular sample, the bacteria becomes the largest entity and so can be separated appropriately from the rest of the fluid.

Mini-Centrifuge:

The centrifuge preferably is constructed using a polymer such as polypropylene, polycarbonate, or Teflon®. The design and principles underlying centrifugation and its use for separating cells and organisms from various matrices is well known. Examples of such information include Industrial centrifugation by Leung [15] Centrifugation in Biology and Medicine [16], and Continuous centrifugation in virus processing [17]. The maximum capacity of the designed centrifuge is intended to be less than about 500 mL. It is a single-use component and is discarded following sample preparation.

The mini-centrifuge has an inlet channel that for introducing the sample into the centrifuge (that is, the channel from the lysis section 105A), an outlet channel for transporting the intact bacteria to the measurement stage 107, and a discharge channel for the rest of the components.

The key variables influencing the efficiency of separation have been described in various well-known texts describing centrifugation processes. The speed of rotation, height of the mini-centrifuge, angle of the walls of the centrifuge from the vertical, and duration of the centrifugation are some of the key variables. These variables can be adjusted routinely by persons skilled in the art to optimize the separation of analyte (such as bacteria) from matrix (such as blood or environmental sample sources).

The centrifuge preferably is rotated by a spindle, which is attached to a motor. The motor in turn is powered by electricity (AC/DC) or by a battery. The preferred power source is a battery.

Infrared Signal Measurement Stage 107:

The spectral region of interest where bacteria have been known to generate characteristic infrared signatures is in the mid-infrared region (about 4000 cm−1 to about 400 cm−1). Spectroscopic methods of analysis generally are known to be rapid and can be automated to test multiple samples at a time. This aspect of spectrometry preferably is utilized in combination with a microfluidic separation stage to enable the detection of bacteria from any sample matrix. The bacteria could be any species of interest. Some samples of bacterial species include *Salmonella* species, *Listeria* species, and *Streptococcus* species.

The primary basis for the detection of the bacteria by the preferred method of detection, FTIR, is the characteristic infrared spectrum of bacteria in general and the difference between species and strains, specifically. The specificity in identification by the devices and associated methods of the present invention is due to the nature of the constituents of the bacterial cell wall—proteins, polysaccharides, nucleic acids, and phospholipids. It is also postulated that other components of the bacteria (such as DNA) and organelles of microorganisms may also contribute to the infrared signature. The composition of the cell wall, for example, affects the intensity and frequencies of the IR absorbance pattern and thus yields characteristic infrared signatures that enable both detection and identification of the different bacteria. In principle, any intact organisms can be distinguished from each other on the basis of their IR signature, provided a satisfactory separation from other components has taken place prior to the measurement and the organism has been sufficiently concentrated as to be above the limit of detection.

The analyte enters the measurement stage 107 via a manifold similar to that described before. At this stage, the analyte largely contains diluent and bacteria. The concentration of the bacteria in the fluid entering the measurement stage 107 preferably is greater than or equal to 10-fold higher than that in the original sample, the volume of the fluid of the original sample is also reduced by an equal or larger amount, and most of the components of the original sample matrix, especially the relatively larger-sized components, are lower (less than about 10-fold) than in the original sample. For example, an initial sample volume of 1 mL may go through the various steps described in the previous sections resulting in bacteria-containing fluid that is concentrated and/or filtered within an area ranging from about 0.01-0.3 mm$^2$. The ability to process a large volume of sample and reduce it to a small area of measurement while recovering most of the bacteria enables detection and identification of the bacteria without culturing. The separation stage (105) plays an important role in isolating the intact bacteria and removing most, if not all, of the substances that might interfere with the infrared signal acquisition. Additional concentration of the bacteria (by the methods described below) in the measurement stage (107) aids in improving the sensitivity of the measurement.

In the preferred embodiment, the intact bacteria following separation as described in 105B flow along a channel (made of the same materials of construction and dimensions as described in section 105A and 105B) until it reaches a zone (referred to as IR measurement zone) where the infrared measurement is made. This zone is constructed using an IR transparent material such as silicon and is positioned so as to be in the infrared beam path.

This zone preferably is a filtration channel fabricated using ultrathin polycrystalline silicon such as the one described by Striemer et al. [18] The aspect ratio of the filter (diameter of pores to thickness of the filter) is approximately 1.0 (the aspect ratio preferably can range from about 0.001 to 100). Flow through this channel enables any remaining small-sized debris and diluent to be filtered leaving the intact bacteria on the surface of the filter. The filtration channel width can range from about 0.1 to 1 mm, while the length can vary from about 0.5 to 5 mm. The pore diameter can range from about 20 nm to 2 microns, though diameters less than about 1 micron are preferred in order to retain a large percentage of bacteria. The use of the ultrathin filter is a critical step since it permits measurement in transmission mode at a good s/n ratio, which improves sensitivity. Conventional filters are too thick and generally have a broad pore distribution. The ultrathin filters have a narrow pore distribution. Together the two features also enable a higher filtration rate, a lower pressure drop, and lower loss of intact bacteria.

Other options, such as an infrared flow cell or an ATR (Attenuated total reflectance) accessory, can also be utilized, as described below.

The measurement stage detects and measures the infrared signature of the bacteria in transmission, attenuated total reflection, reflection, and other modes and consists of the spectrometer (source and detector), flow cell or detection window, interface to provide digitized data for analysis, and a waste collection stage.

The measurement itself is made in a manner similar to that used for infrared measurements for different applications such as analytical and forensics (for example, trace residues, environmental contaminants, etc.). The instrument relies on interferometry to acquire an interferogram, which is then subjected to Fourier transformation to yield the spectrum in the frequency domain. This type of data acquisition has been well described in many textbooks on the subject of infrared spectroscopy such as Griffiths [19].

The source and detector and interface to provide digitized data for analysis is similar to that utilized in other infrared spectrometers. The detector may also be a detector array (described below). The source may be a regular thermal source or a laser-based source and may utilize coherent or incoherent radiation that is capable of emitting radiation over the range from about 400 to 4000 cm−1.

The fluid from the separation stage may be diluted using a non-aqueous infrared transparent solvent. This could be performed to reduce the effect of the infrared signal due to water depending on the desired signal-to-noise (sn) ratio.

When the ultrathin filter is used, this step can be avoided since most, if not all, of the signal due to water is eliminated due to removal of water by the filter.

The bacteria-containing fluid (bacfluid) can be readied for measurement in multiple ways—filtration followed by measurement of the bacteria retained on the surface of the filter (preferred option), flow past the IR sensing zone (IR sensing zone option), flow through a flow cell (flow cell option), or use of an ATR (ATR option). In all cases, there is either spatial or temporal (or both) resolution of the sample enabling discrimination between signals from different bacteria as well as between bacteria and the background. Previous attempts, such as Helm et al. [1], [20], to measure IR spectra of bacteria did not possess any of the components described in this invention and consequently measured the weighted average of all signals. This resulted in the need for large amounts of highly purified bacteria (greater than about $10^4$ CFU/mL). The approach described in this invention does not require such a large quantity of bacteria as in prior approaches and devices, and also provides a higher sensitivity. Various different options for alternative embodiments are described below.

In the case of filtration, the bacteria-containing fluid (referred to as bacfluid) is passed through an IR-compatible filter (such as ultrathin silicon/silicon nitride filters from SimPore or polyethylene filters from Millipore) that has a pore size less than about 0.5 microns (preferred size is about 0.2 microns or less). The bacteria are retained by the filter while those components that were smaller than the bacteria and not eliminated by the separation stage will pass through the filter. This filter is referred to as the bacteria filter.

The filter may be of any shape (rectangular, circular, etc.) covering an area ranging from about 100 micron squared to about 10 centimeters squared.

The bacteria on the filter are illuminated by the IR light source (for example, by globar, tungsten filaments, or lasers from Block Engineering or Lasnix) while the readout is performed using a single point detector or an array detector. The single-point detector provides the weighted average of the infrared signals in the measurement area (e.g. about 100×100 micron). The detector array is arranged such that it covers the entire surface of the filter. Infrared radiation from specific locations of the filter surface is gathered by the array providing spatial resolution and a spectroscopic image of the filter surface. This, in turn, enables better discrimination of the bacteria from the filter surface and other moieties that may be on the filter surface. The array can be about 1×1 to about 1024×1024. The detection can measure either the near-field far-field infrared signals.

A reference filter may be utilized in order to obtain a background spectrum. This reference filter is placed after the first filter and is identical with respect to size, dimension, and material of construction. The fluid that passed through the bacteria filter passes through the reference filter as well.

The IR sensing zone preferably is made of silicon and integrated with the exit channel from the separation section 105B. The measurement preferably is made in transmission mode. The silicon may be coated with anti-reflective coating to improve the transmission percentage. Alternatively, silicon crystals to enable ATR measurements may also be utilized as will be known to persons skilled in the art. The methods of integrating the IR sensing zone to perform FTIR measurements is well known and has been described earlier for monitoring reactions in microreactors. [21-23]

The exiting fluid can flow through the IR sensing zone (Flow through measurements) or may be analyzed in batch mode. In batch mode measurements, the fluid is typically introduced as tiny droplets (volume ranging from about 1 nanoliter to about 100 microliters). These droplets are dried either by flowing a drying gas such as nitrogen or by allowing for environmental conditions to permit drying. The result is that the bacteria form a thin film (ideally a monolayer) on the surface of the IR sensing zone with little to no contribution from water in the IR spectrum. Such a thin film can be analyzed in transmission mode or using alternative measurement modes such as ATR, DRIFT, etc. Such methods of spotting or microprinting of bacteria is well known [24]. However, earlier approaches utilized pure culture for such spotting, whereas this invention seeks to eliminate the need for pure culture.

The sensing zone area ranges from about 2-50 millimeters in length, about 10 to 500 microns in width, and about 6 to 1000 microns in height.

Flow-Through Measurements:

In this case the bacfluid flows through a channel at a fixed velocity while transiting the detection window. The channel can be etched onto a sample accessory (such as ATR) or may be constructed using known IR-transparent materials (such as zinc selenide or silicon). The means to construct an ATR accessory and obtain infrared measurements using this accessory is well known ([25] and [26]). The difference in this invention is that microchannels are imprinted on the surface of the ATR using IR-transparent materials so that the fluid moves along a fixed path. The ATR itself is constructed using established methods and techniques. The microchannel path on the surface of the ATR can be a straight channel, a curved path, a sawtooth pattern, or any pattern. Methods of preparing such imprinted microchannels have been described previously [27] and [28]. The width of the channel must be greater than 50 microns to enable the bacteria to move through the channels. Data acquisition is not affected by this change.

In another embodiment, the channel is manufactured by microboring a path in an IR transparent material such as calcium fluoride and from a single piece. The latter requirement is to ensure that the interior surface is continuous without any cracks or deformities. The fluid flow path is a straight path through the IR cell though other forms such as curved or saw tooth patterns are possible. An example of the construction of the flow cell and its use in acquiring data is provided by U.S. Pat. No. 5,521,384 [29] and U.S. Pat. No. 4,618,769 [30].

The IR measurement can occur either at a fixed location in the flow channel or may cover a region of the flow channel. In either case, the bacfluid is illuminated by the IR light source while the readout is performed using a detector array. The array can be about 1×1 to about 1024×1024. The detection can measure either the near-field or the far-field infrared signals. This approach also enables background signal measurement, resolution between background and sample signals as well as signals from different bacteria.

Spectral Analysis Stage 109:

The spectral analysis is performed using a processor (or multiple processors) along with associated software. The software, in the preferred embodiment, subtracts the background spectrum, compensates for the presence of atmospheric carbon dioxide and water vapor. The intensities at each wavelength are used to create a matrix of values from which various attributes are identified and utilized in the analysis described below. The attributes include peak maxima positions, peak widths at specific wavelengths, peak minima positions, and positions of minimum peak intensity. These attributes are also used in the comparison against spectra in the reference database to determine the closest match to the acquired spectra. Such spectral analysis and comparisons are being commonly utilized in various applications such as biometric identification, peptide map comparisons, vegetation mapping, etc. In the preferred embodiment, this analysis is performed automatically without any manual intervention. However, the option to conduct a manual verification of the analysis and conduct other assessments is provided.

Appropriate data technology is discussed below and in various reference materials that are identified in this specification. It is contemplated that the processor may be part of a discrete computer device or system or may be part of the device hardware, or is a combination of both, or is otherwise accessible for purposes of the present invention. The software consists of a set of computer-executable instructions and may also include data structures capable of storing spectral information. The software may be part of a computer, part of the device hardware, or a combination of both. These components are quite well known and commonly utilized in acquiring data from various instruments. Examples describing such systems can be found in [31], [32], and [33].

The data structure for a spectrum typically consists of the interferogram and its Fourier transformed version. The Fourier transformed data set normally consists of intensity measured at each wavelength and enables one to trace the spectrum similar to the spectrum shown in FIG. 2. Additional attributes of the spectrum such as baseline noise, width of peaks, second derivative, and other mathematical transformations may also be stored as part of the data structure for a sample. Normally the data structure is an "m×n" matrix where the "m" rows represent the number of wavelengths where measurements were made and the "n" columns represent the different attributes of interest.

The data structures can also be part of a database management system with the option to search, query, and retrieve spectral information. The database management systems can be any of the well-known systems such as MySQL, Oracle, Microsoft Access, etc. The information stored in the data structures normally contains spectral information of different bacterial species in different matrices.

Preferably, two (or more) databases are utilized. One of the databases is a reference database, which contains spectral information of bacterial reference standards acquired under controlled conditions. The information in this database is used as a training set for validating the model as well as for comparison purposes. Databases available at sources such as the Institute for Microbiology at Munich Technical University are utilized and may be augmented with new information gathered by the user for the above purpose. The information in these databases identifies factors that contribute towards predictive modeling for determining the identity of the bacteria. Predictive models are based on data cluster investigation techniques such as principal component analysis (PCA), and hierarchical cluster analysis (HCA) and on classification algorithms such as K-nearest neighbors (KNN) and soft independent modeling of class analogy (SIMCA). Such techniques are routinely utilized by commercially available software such as PIROUETTE and JMP. Following training using known bacteria, the predictive model is validated using additional known bacteria before utilizing the model for analyzing samples where the presence of bacteria and their identity, if present, are not known. In the preferred embodiment, the reference database is provided along with the instrument. In addition, the validation using the reference database and a predictive model are also provided. The user has the option to update or modify the reference database and validation model. It is expected that this might generally be done as the user obtains the spectra of additional bacterial species and strains or if the user has bacterial standards that may not be part of the original reference database.

The second database is typically a sample database that can vary from user to user and contains spectral information of all samples analyzed along with information such as date and time of acquisition, location, sample ID, analyst, and any sample other tracking information desired by the user. This database is utilized for trend analysis, review of results and preferably be maintained, backed up, and updated by the user. The user may choose to maintain different databases for the different departments, divisions, or laboratories. Thus, multiple sample databases may exist at a user site or on the device itself.

If the carrier solvent that is not water is utilized, one means to rapidly screen for the presence of bacteria is to screen for the presence of a characteristic "water" peak spikes in the sample. The water peak arises owing the presence of water within the bacteria and because this concentration of water is different from that of the surrounding solvent.

The first step in the analysis is the subtraction of the background spectrum. In the case of the detector array, this will be a region without any absorbance in the regions where bacteria might absorb or a spectrum obtained from the reference filter. In the case of the flow through measurement, this will be a region without any substantial absorbance in the regions where bacteria might absorb.

Following identification and subtraction of the background spectrum from the sample spectrum, the analysis (performed by the software) determines if the spectrum possesses features that are common to all bacteria. These include possessing absorbance in the five major absorbance regions in an IR spectrum. These are about 3000-2800 cm−1 (region 1), about 1700-1500 cm−1 (region 2), about 1500-1200 cm−1 (region 3), about 1200-900 cm−1 (region 4), and about 900-700 cm−1 (region 5). Region 5 is the fingerprint region that contains weak but very unique absorbances that are characteristic to specific bacteria.

If the levels of bacteria in the sample are low, the absorbance intensities will be low (despite the separation and enrichment). Therefore, each result determination made be the software may be accompanied with a probability estimate that the result is accurate. The probability estimates are based on the predictive modeling software (the classification algorithms), which assess the similarity of the spectral parameters of the unknown sample to that of the known samples. Some of the approaches utilized for predictive modeling were described earlier. Typically the algorithms used for such modeling compute an index that measure the similarity of the data for the unknown sample to a benchmark. Examples of such indices include the Rand measure, F-measure, and Jaccard index. The indices normally serve as a measure of the percentage of correct decisions made by the algorithm. In the preferred embodiment, the index reports the measure of the correct decisions made balanced by the contribution of false negatives during the validation of the model. The estimate may be a number or represented by a color code, or graph. Typically, the expected probability for reporting a positive result is greater than about 60%, while greater than about 90% is preferred.

Once bacterial presence in the sample is ascertained, the software proceeds to the next step in the analysis. If no bacteria are determined to be present, the analysis terminates and the result is provided to the user.

The next step in the analysis is the determination if the bacteria are gram positive or gram negative. Gram-positive bacteria possess a higher level of peptidoglycan (greater than about 50%) compared to gram-negative bacteria. In addition, they also possess teichoic acids and lower lipid, protein, and lipopolysaccharide content. These differences result in an infrared signature that is different from the gram-negative bacteria. If needed, the spectrum may also be compared against a reference spectrum of gram positive and gram-negative bacteria. The reference spectrum is normally stored as a data structure, which could be part of the device hardware, a local computer, or stored on a server. During the comparison, the software queries the database and searches the data structures containing the spectra of bacteria (or other analyte) looking for the closest match to the spectrum of the sample. The comparisons are based on the intensity, frequency, and width of the infrared absorption bands typically. If a match is found, the reference spectrum that matches the sample spectrum is temporarily flagged in case a review by the user is needed. The recently acquired sample spectrum is added to the sample database and utilized in various analyses such as trend analysis at the user's discretion.

As before, the determination regarding gram positive or gram negative may be accompanied with a probability estimate concerning the accuracy of the result. In case a suitable distinction between gram positive and gram negative cannot be made, the result being reported as being potentially gram variable or indeterminate. The expected probability for classification as gram positive or negative is greater than about 60% while greater than about 90% is preferred.

Following this stage of analysis, the next stage is the identification of the species. In this case, spectral information is evaluated using the predictive modeling described earlier. In addition, the spectrum will be compared against the individual species that are in the database. An efficient search algorithm that enables comparison of the sample spectrum against the reference spectra is utilized to determine the identity. If a suitably high degree of match (greater than about 70%, while greater than about 90% is preferred) with a reference spectrum is achieved, the probable identity of the bacteria is reported along with the estimated probability of result accuracy.

Sample can be compared directly against the spectrum of a reference bacteria sample through visual examination or compared after standard deconvolution techniques that are well known and frequently utilized in FTIR data analysis (such as Gaussian deconvolution or second derivative analysis) and which have been described by reports and books such as [19], [34], [35]. Second derivative analysis for instance, is used to determine the position (for example, wavenumber) of peaks (usually poorly resolved peaks). The positions of these peaks are compared against the reference to determine the closeness of match. The comparison of the sample spectrum against the reference spectrum is performed as described earlier. To ensure reproducibility in identification, combinations of the above approaches may be utilized.

Result Reporting Stage 111:

The results (presence of bacteria, gram staining classification, and identity) are transmitted to the desired output format—on screen, USB, text message, and/or other peripheral devices such as a printer. The parameters involved in the analysis along with the original data and estimations are stored on the local hard drive or transmitted to a secure location of the user's choosing. In industries where needed, a feature that tracks edits, analyst, and other pertinent information (referred to as "audit track") is also provided.

Computer Systems:

Implementations of the various techniques described herein may be implemented in digital electronic circuitry, or in computer hardware, firmware, software, or in combinations of them. Implementations may implemented as a computer program product, for example, a computer program tangibly embodied in an information carrier, for example, in a machine-readable storage device or in a propagated signal, for execution by, or to control the operation of, data processing apparatus, for example, a programmable processor, a computer, or multiple computers. A computer program, such as the computer program(s) described above, can be written in any form of programming language, including compiled or interpreted languages, and can be deployed in any form, including as a stand-alone program or as a module, component, subroutine, or other unit suitable for use in a computing environment. A computer program can be deployed to be executed on one computer or on multiple computers at one site or distributed across multiple sites and interconnected by a communication network.

Method steps may be performed by one or more programmable processors executing a computer program to perform functions by operating on input data and generating output. Method steps also may be performed by, and an apparatus may be implemented as, special purpose logic circuitry, for example, an FPGA (field programmable gate array) or an ASIC (application-specific integrated circuit).

Processors suitable for the execution of a computer program include, by way of example, both general and special purpose microprocessors, and any one or more processors of any kind of digital computer. Generally, a processor will receive instructions and data from a read-only memory or a random access memory or both. Elements of a computer may include at least one processor for executing instructions and one or more memory devices for storing instructions and data. Generally, a computer also may include, or be operatively coupled to receive data from or transfer data to, or both, one or more mass storage devices for storing data, for example, magnetic, magneto-optical disks, or optical disks. Information carriers suitable for embodying computer program instructions and data include all forms of non-volatile memory, including by way of example semiconductor memory devices, for example, EPROM, EEPROM, and flash memory devices; magnetic disks, for example, internal hard disks or removable disks; magneto-optical disks; and CD-ROM and DVD-ROM disks. The processor and the memory may be supplemented by, or incorporated in special purpose logic circuitry.

To provide for interaction with a user, implementations may be implemented on a computer having a display device, for example, a cathode ray tube (CRT) or liquid crystal display (LCD) monitor, for displaying information to the user and a keyboard and a pointing device, for example, a mouse or a trackball, by which the user can provide input to the computer. Other kinds of devices can be used to provide for interaction with a user as well; for example, feedback provided to the user can be any form of sensory feedback, for example, visual feedback, auditory feedback, or tactile feedback; and input from the user can be received in any form, including acoustic, speech, or tactile input.

Implementations may be implemented in a computing system that includes a back-end component, for example, as a data server, or that includes a middleware component, for example, an application server, or that includes a front-end component, for example, a client computer having a graphical user interface or a Web browser through which a user can interact with an implementation, or any combination of such back-end, middleware, or front-end components. Components may be interconnected by any form or medium of digital data communication, for example, a communication network. Examples of communication networks include a local area network (LAN) and a wide area network (WAN), for example, the Internet.

Example 1

In one embodiment of the device to determine the identity of a pathogenic bacteria in blood, the microfluidic separation stage is as described in FIG. 3. Whole blood is diluted using water about ten-fold and enters the microfluidic chip. The amount of blood cells (white blood cells, red blood cells, and platelets) is reduced using the blood cell reducer using the inertial forces generated by the spiral flow path. While most of the blood cells are eliminated as a waste stream, the intact bacteria, some blood cells, other non-bacterial cells of similar size to the intact bacteria, and plasma move to the next sub-stage—the porous polymer monoliths. The blood cells entering this stage and other non-bacterial cells are selectively lysed taking advantage of their higher sensitivity to mechanical stresses yielding a fluid stream that consists of intact bacteria, lysis debris, and plasma. This fluid stream moves to the DLD sub-stage where the intact bacteria are separated from the rest of the components on the basis of the difference in their hydrodynamic size. The volume of the fluid containing the intact bacteria is reduced by about 10-10000-fold during this sub-stage. This small volume of fluid containing intact bacteria and plasma proteins next moves to the nanofilter. The plasma proteins pass through the pores of the filter along with water and other small molecules (for example, glucose, cholesterol, and the like) leaving the intact bacteria on the surface of this nanofilter. The surface area of the filter is about 0.01-0.3 mm$^2$. Processing a 1 mL sample volume at 10 CFU/mL in the manner described above leads to an effective concentration of $10^6$ CFU/mL at time of measurement assuming 100% recovery of intact bacteria, measurement area of 0.01 mm$^2$, and a film thickness of 1 micron.

By processing a relatively large volume (1 mL) of blood, the probability (and the amount of) bacterial presence in the sample is increased. Since bacteria are not distributed homogeneously throughout the clinical sample, a 0.1 mL sample of blood is not assured of containing 1 CFU of bacteria. The concentration of the intact bacteria enables identification without requiring culturing and isolation.

The infrared spectrum is collected using an FTIR spectrometer such as the Vertex 80 ® from Bruker equipped with a microscope accessory such as the Hyperion® (Bruker). This is typically performed at about a 4 cm$^{-1}$ resolution. The background spectrum is first collected using nanofilter before bacterial concentration as the background. The spectrum of the bacteria on the nanofilter surface (sample spectrum) is acquired. The background spectrum and atmospheric contributions (such as those due to carbon dioxide and water vapor) are then subtracted from this sample spectrum. The second derivative of the resulting spectrum is then acquired to determine the position of the peaks over the range from about 400 to 4000 cm$^{-1}$. The position of the peaks is represented by the local minima of the second derivative of the spectrum. These positions are compared against those in the reference database. In addition, the matrix of the sample spectrum (after subtraction of the background and atmospheric contributions) consists of the wavenumber and intensity of absorbance at each wavenumber. These spectral profiles are also further smoothed using a 9-point Savitzky-Golay algorithm.

Cluster analysis is conducted according to Ward's algorithm [36]. In this method, the criterion for choosing the pair of clusters to merge at each step is based on the optimal value of an objective function, such as the error of the sum of squares. At each step of the analysis, clusters of data with the minimum inter-cluster distance are merged. This assessment is used to classify the different pathogens and the resulting method was stored in a database. The sample spectrum is analyzed against this database to determine which of the pathogenic spectra it most closely resembles. This is reported as the identity of the bacteria.

Example 2

The presence and identification of bacteria in a pharmaceutical-containing solution such as a monoclonal antibody biopharmaceutical preparation is determined by the detection system as generally described above. The microfluidic separation stage resembles the one shown in FIG. 3. However, the blood cell reducer sub-stage is removed from the microfluidic chip. Very few non-bacterial cells are expected in such a sample. Despite this, the sample stream is made to flow through the lysis stage. Any non-bacterial cells present would be selectively lysed yielding intact bacteria, lysis debris, and pharmaceutical-containing solution.

This fluid stream moves to the lysis-debris remover sub-stage where the intact bacteria are separated from the rest of the components on the basis of the difference in their hydrodynamic size. Most of the pharmaceutical product is separated from the intact bacteria along with any lysis debris. The volume of the fluid containing the intact bacteria is reduced by about 10-10000-fold during this sub-stage. This small volume of fluid containing intact bacteria moves to the nanofilter. Any residual component (for instance, formulation components such as buffering agent) is filtered, leaving the intact bacteria on the surface of this nanofilter. The bacteria on the surface of this nanofilter are identified as described in Example 1.

Example 3

Bacterial contamination of milk is ascertained by the detection system. In this case, milk is diluted using water about 10-fold and enters the microfluidic chip. The concentration of the proteins, fats, and other components of milk is reduced by dilution and by passage through a spiral path. This configuration is the similar to the one shown in FIG. 3. Inertial forces are used to reduce the level of components smaller than the bacteria; the bacteria-containing stream is directed towards the lysis sub-stage while the rest of the stream is directed to a waste receptacle. The lysis sub-stage is used to lyse any non-bacterial cells (for instance, epithelial cells from a cow) leaving intact bacteria to pass onto the lysis debris removal stage. In this embodiment, the lysis debris removal stage is also a spiral flow path that separates the lysis debris from bacteria on the basis of their hydrodynamic size. The intact bacteria-containing solution is collected on the surface of an IR-compatible surface, such as zinc selenide, and allowed to dry. The surface of the zinc selenide is then mapped using an array detector. Areas, containing distinctive bacterial absorbance patterns are identified and the bacterial signature compared against the reference database as described before. If no bacterial absorbance patterns are identified, the absence of bacteria in the sample is reported as the result.

The invention described in this specification generally relates to devices and associated methods of detecting and identifying microorganisms such as bacteria and other small and very small multicellular microorganisms. While certain exemplary embodiments have been described above in detail and shown in the accompanying drawing figures, it is to be understood that such embodiments and examples are merely illustrative of and not restrictive of the broad invention. In particular, it should be recognized that the teachings of the invention apply to variations of the preferred embodiments that are specifically discussed.

While certain features of the described implementations have been illustrated as described herein, many modifications, substitutions, changes and equivalents will now occur to those skilled in the art. Thus, it will be understood that the invention is not limited to the particular embodiments or arrangements disclosed, but is rather intended to cover any changes, adaptations or modifications which are within the scope and spirit of the invention as defined by the appended claims.

REFERENCES

All of the journal articles and all other publications, patents and texts mentioned in this specification are incorporated by reference in their entireties, including the following:

[1] D. Helm, H. Labischinski, G. Schallehn and D. Naumann, "Classification and identification of bacteria by Fourier-transform infrared spectroscopy", *J Gen Microbiol*, 137, no. 1, p. 69-79, 1991.

[2] M. El-Sayed and I. H. El-Sayed, "United States Patent, U.S. Pat. No. 6,379,920", United States Patent, U.S. Pat. No. 6,379,920, no., 2002.

[3] Y. Cinar, G. Demir, M. Pa∈ and A. B. Cinar, "Effect of hematocrit on blood pressure via hyperviscosity", *Am J Hypertens*, 12, no. 7, p. 739-43, 1999.

[4] A. M. Streets and Y. Huang, "Chip in a lab: Microfluidics for next generation life science research", *Biomicrofluidics*, 7, no. 1, p. 11302, 2013.

[5] G. S. Fiorini and D. T. Chiu, "Disposable microfluidic devices: fabrication, function, and application", *Biotechniques*, 38, no. 3, p. 429-46, 2005.

[6] G. S. Fiorini, M. Yim, G. D. M. Jeffries, P. G. Schiro, S. A. Mutch, R. M. Lorenz and D. T. Chiu, "Fabrication improvements for thermoset polyester (TPE) microfluidic devices", *Lab Chip*, 7, no. 7, p. 923-6, 2007.

[7] B. Adler, T. Laurell and S. Ekström, "Optimizing nanovial outlet designs for improved solid-phase extraction in the integrated selective enrichment target—ISET", *Electrophoresis*, 33, no. 21, p. 3143-50, 2012.

[8] J. Sun, M. Li, C. Liu, Y. Zhang, D. Liu, W. Liu, G. Hu and X. Jiang, "Double spiral microchannel for label-free tumor cell separation and enrichment", *Lab Chip*, 12, no. 20, p. 3952-60, 2012.

[9] L. R. Huang, E. C. Cox, R. H. Austin and J. C. Sturm, "Continuous particle separation through deterministic lateral displacement", *Science*, 304, no. 5673, p. 987-90, 2004.

[10] D. W. Inglis, N. Herman and G. Vesey, "Highly accurate deterministic lateral displacement device and its application to purification of fungal spores", *Biomicrofluidics*, 4, no. 2, 2010.

[11] J. Takagi, M. Yamada, M. Yasuda and M. Seki, "Continuous particle separation in a microchannel having asymmetrically arranged multiple branches", *Lab on a Chip*, 5, no. 7, p. 778-784, 2005.

[12] M. Yamada and M. Seki, "Microfluidic particle sorter employing flow splitting and recombining", *Anal Chem*, 78, no. 4, p. 1357-62, 2006.

[13] D. W. Inglis, J. A. Davis, R. H. Austin and J. C. Sturm, "Critical particle size for fractionation by deterministic lateral displacement", *Lab Chip*, 6, no. 5, p. 655-8, 2006.

[14] K. K. Zeming, S. Ranjan and Y. Zhang, "Rotational separation of non-spherical bioparticles using I-shaped pillar arrays in a microfluidic device", *Nat Commun*, 4, no., p. 1625, 2013.

[15] W. W.-F. Leung, *Industrial centrifugation technology*, no. New York: McGraw-Hill, 1998.

[16] P. Sheeler, *Centrifugation in biology and medical science*, no. New York: Wiley, 1981.

[17] W. C. Patrick and R. R. Freeman, "Continuous centrifugation in virus processing", *Journal of Biochemical and Microbiological Technology and Engineering*, 2, no. 1, p. 71-80, 1960.

[18] C. C. Striemer, T. R. Gaborski, J. L. McGrath and P. M. Fauchet, "Charge- and size-based separation of macromolecules using ultrathin silicon membranes", *Nature*, 445, no. 7129, p. 749-53, 2007.

[19] P. R. Griffiths and J. A. De Haseth, *Fourier transform infrared spectrometry*, no. New York: Wiley, 1986.

[20] M. M. Mossoba, S. F. Al-Khaldi, S. K. Curtis, C. F. Battrell and F. S. Fry, "Application of a novel hydrophilic infrared-transparent membrane to the differentiation between microcolonies of *Enterobacter sakazakii* and *Klebsiella pneumoniae*", *J Food Prot*, 70, no. 5, p. 1241-5, 2007.

[21] K. Geyer, J. D. Codée and P. H. Seeberger, "Microreactors as Tools for Synthetic Chemists The Chemists' Round-Bottomed Flask of the 21st Century?", *Chemistry—A European Journal*, 12, no. 33, p. 8434-8442, 2006.

[22] R. Herzig-Marx, K. T. Queeney, R. J. Jackman, M. A. Schmidt and K. F. Jensen, "Infrared spectroscopy for chemically specific sensing in silicon-based microreactors", *Anal Chem*, 76, no. 21, p. 6476-83, 2004.

[23] T. M. Floyd, M. A. Schmidt and K. F. Jensen, "A silicon microchip for infrared transmission kinetics studies of rapid homogeneous liquid reactions", in *Micro Total Analysis Systems* 2001, 2001, no., p. 277-279 "A silicon microchip for infrared transmission kinetics studies of rapid homogeneous liquid reactions", in *Micro Total Analysis Systems* 2001, no., 2001, p. 277-279.

[24] S. Al-Khaldi, M. Mossoba, A. Ismail and F. Fry, "Accelerating bacterial identification by infrared spectroscopy by employing microarray deposition of microorganisms", *Foodborne Pathogens and Disease*, 1, no. 3, p. 172-177, 2004.

[25] C. Wood and I. Alcock, "U.S. Pat. No. 6,414,311", U.S. Pat. No. 6,414,311, no., 2002.

[26] P. J. Melling and M. A. Thomson, "United States Patent 20130037719", United States Patent 20130037719, no., 2013.

[27] K. L. A. Chan, X. Niu, A. J. de Mello and S. G. Kazarian, "Rapid prototyping of microfluidic devices for integrating with FT-IR spectroscopic imaging", *Lab Chip*, 10, no. 16, p. 2170-4, 2010.

[28] J.-Y. Cheng, C.-W. Wei, K.-H. Hsu and T.-H. Young, "Direct-write laser micromachining and universal surface modification of PMMA for device development", *Sensors and Actuators B: Chemical*, 99, no. 1, p. 186-196, 2004.

[29] D. C. Lynch, "U.S. Pat. No. 5,521,384", U.S. Pat. No. 5,521,384, no., 1996.

[30] C. C. Johnson and L. T. Taylor, "U.S. Pat. No. 4,618,769", U.S. Pat. No. 4,618,769, no., 1986.

[31] "Wikipedia", *Wikipedia*, no.

[32] S. S. Young, *Computerized data acquisition and analysis for the life sciences: a hands-on guide*, no. Cambridge, UK; New York, NY: Cambridge University Press, 2001.

[33] M. Abdallah and O. Elkeelany, "Simultaneous Multichannel Data Acquisition and Storing System", in *Computing, Engineering and Information, 2009. ICC'09. International Conference on*, 2009, no., p. 233-236 "Simultaneous Multi-channel Data Acquisition and Storing System", in *Computing, Engineering and Information, 2009. ICC'09. International Conference on*, no., 2009, p. 233-236.

[34] D.-W. Sun, "Infrared spectroscopy for food quality analysis and control", *Infrared spectroscopy for food quality analysis and control*, no. Elsevier/Academic, Amsterdam; London, 2009.

[35] B. C. Smith, *Fundamentals of Fourier transform infrared spectroscopy*, no. Boca Raton, FL: CRC Press, 2011.

[36] J. J. Ward, "Hierarchical grouping to optimize an objective function", *Journal of the American Statistical Association*, 58, no., p. 236-244, 1963.

The invention claimed is:

1. A detection system for identifying microorganisms within a sample, the sample comprising a fluid and including non-microbial cells and microorganisms, the detection system comprising:
   a microfluidic separation stage comprising a lysis structure that includes an inlet, an outlet, and microporous surfaces disposed between the inlet and the outlet to receive the sample and selectively lyse non-microbial cells while maintaining intact microorganisms in the sample when the sample flows between the inlet and the outlet and through the microporous surfaces of the lysis structure;
   a detection stage to receive the sample from the microfluidic separation stage and perform detection analysis of microorganisms in the sample.

2. The detection system of claim 1, wherein the microorganisms are selected from the group consisting of bacteria, fungi, and small unicellular and multicellular organisms.

3. The detection system of claim 1, wherein the sample is a liquid selected from the group consisting of whole blood, plasma, serum, saliva, urine, cerebrospinal fluid, water, and fruit and vegetable juices.

4. The detection system of claim 1, wherein the sample is selected from the group consisting of a fluid derived from meat, produce, processed food, dairy products, poultry products, pharmaceutical process streams, bulk drug substance, and final drug product.

5. The detection system of claim 1, wherein the volume of the sample ranges from about 0.1 mL to about 10 mL.

6. The detection system of claim 1, wherein the microfluidic separation stage further comprises:
   a first separation stage to separate components that are larger in size than the microorganisms for detection, wherein the lysis structure receives the sample from the first separation stage at the inlet of the lysis structure; and
   a second separation stage to receive the sample from the outlet of the lysis structure, the second separation stage to separate lysed cells and cellular debris from the microorganisms for detection.

7. The detection system of claim 1, wherein the microfluidic separation stage concentrates the microorganisms in the sample by a process selected from the group consisting of reduction in total sample volume and filtration.

8. The detection system of claim 1, further comprising:
   an identification stage to identify intact microorganisms based upon the detection analysis.

9. The detection system of claim 8, wherein the identification stage further comprises a measurement stage that measures the signatures of the microorganisms in transmission mode.

10. The detection system of claim 9, wherein the measurement stage further comprises a flow cell or detection window.

11. The detection system of claim 9, wherein the measurement stage comprises polycrystalline silicon.

12. The detection system of claim 9, wherein the identification stage further comprises a computer system.

13. The detection system of claim 9, wherein the identification stage further comprises a reporting stage.

14. The detection system of claim 1, further comprising a waste collection stage.

15. The detection system of claim 1, further comprising a control stage.

16. The detection system of claim 1, wherein the microorganisms are selected from the group of genera consisting of *Staphylococcus, Escherichia, Listeria, Salmonella, Streptococcus, Klebsiella* and *Campylobacter*.

17. The detection system of claim 1, wherein the detection system is portable.

18. The detection system of claim 1, wherein the microporous surfaces are sized to permit passage of intact microorganisms in the sample through the microporous surfaces while lysing non-microbial cells.

19. The detection system of claim 1, wherein the microporous surfaces include pores having diameters from 1 micrometer to 10 micrometers.

20. The detection system of claim 1, wherein the lysis structure comprises at least one porous monolithic structure disposed between the inlet and the outlet of the microfluidic separation stage, and the porous monolithic structure includes the microporous surfaces.

* * * * *